(12) United States Patent
Young et al.

(10) Patent No.: US 9,169,479 B2
(45) Date of Patent: *Oct. 27, 2015

(54) MICROFLUIDIC DEVICE-BASED NUCLEIC ACID PURIFICATION METHOD

(71) Applicant: RHEONIX, INC., Ithaca, NY (US)

(72) Inventors: Lincoln C. Young, Ithaca, NY (US); Peng Zhou, Newtown, PA (US); Gwendolyn Spizz, Ithaca, NY (US); Rubina Yasmin, Ithaca, NY (US)

(73) Assignee: RHEONIX, INC., Ithaca, NY (US)

( * ) Notice: Subject to any disclaimer, the term of this patent is extended or adjusted under 35 U.S.C. 154(b) by 6 days.

This patent is subject to a terminal disclaimer.

(21) Appl. No.: 14/226,204

(22) Filed: Mar. 26, 2014

(65) Prior Publication Data

US 2014/0206009 A1    Jul. 24, 2014

Related U.S. Application Data

(62) Division of application No. 13/400,857, filed on Feb. 21, 2012, now Pat. No. 8,722,329.

(60) Provisional application No. 61/444,952, filed on Feb. 21, 2011.

(51) Int. Cl.
*C12Q 1/68* (2006.01)
*C12N 15/10* (2006.01)

(52) U.S. Cl.
CPC .......... *C12N 15/1013* (2013.01); *C12Q 1/6806* (2013.01)

(58) Field of Classification Search
CPC .......................... C12N 15/1013; C12Q 1/6806
USPC .................................................. 435/91.2, 6.1
See application file for complete search history.

(56) References Cited

U.S. PATENT DOCUMENTS 8,722,329 B2 * 5/2014 Young et al. .................. 435/6.1
2009/0253181 A1 * 10/2009 Vangbo et al. ............... 435/91.1

* cited by examiner

*Primary Examiner* — Cynthia B Wilder
(74) *Attorney, Agent, or Firm* — William Greener; Blaine T. Bettinger; Bond, Schoeneck & King, PLLC

(57) ABSTRACT

A method is provided for purifying nucleic acid from a sample in a microfluidic device. The method can be used to purify nucleic acids from any source known in the art that comprises nucleic acids, such as prokaryotic or eukaryotic organisms, viruses, cell, tissues, organs, etc. In a specific example, the tissue is whole blood. The method for purifying nucleic acid may run fully automated in the microfluidic device.

16 Claims, 15 Drawing Sheets

Fig. 1 Flow Diagram
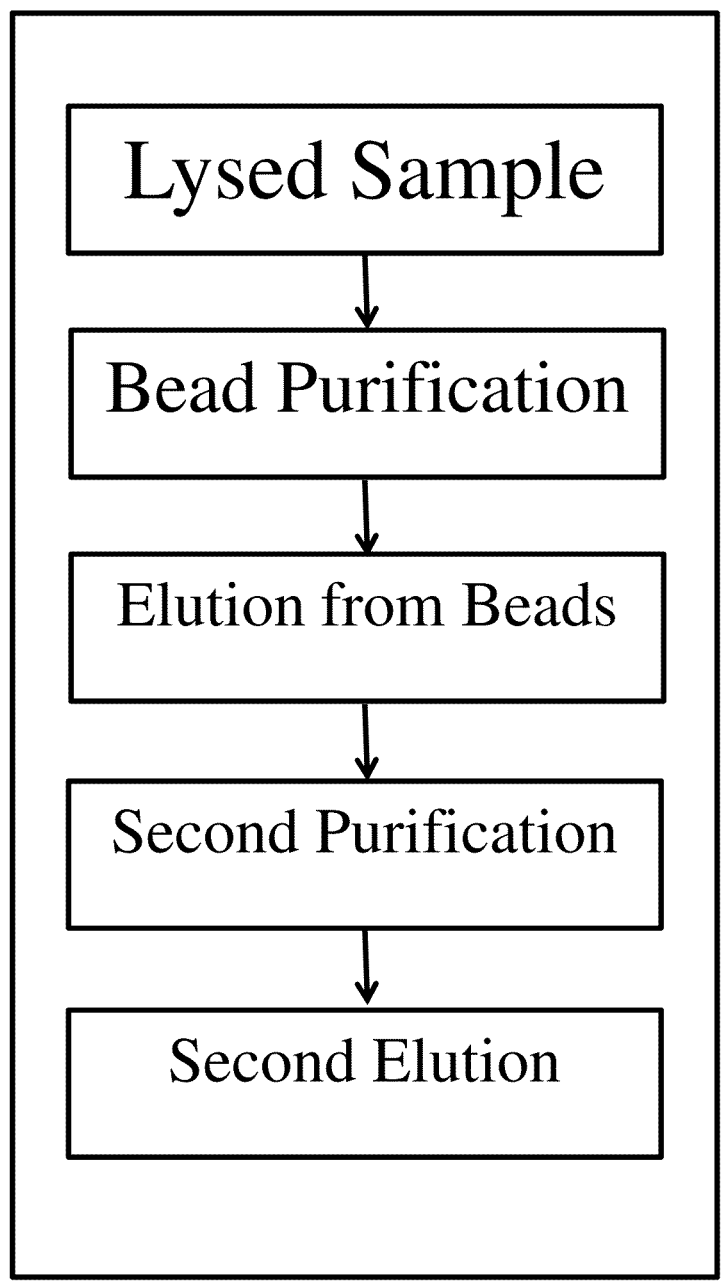

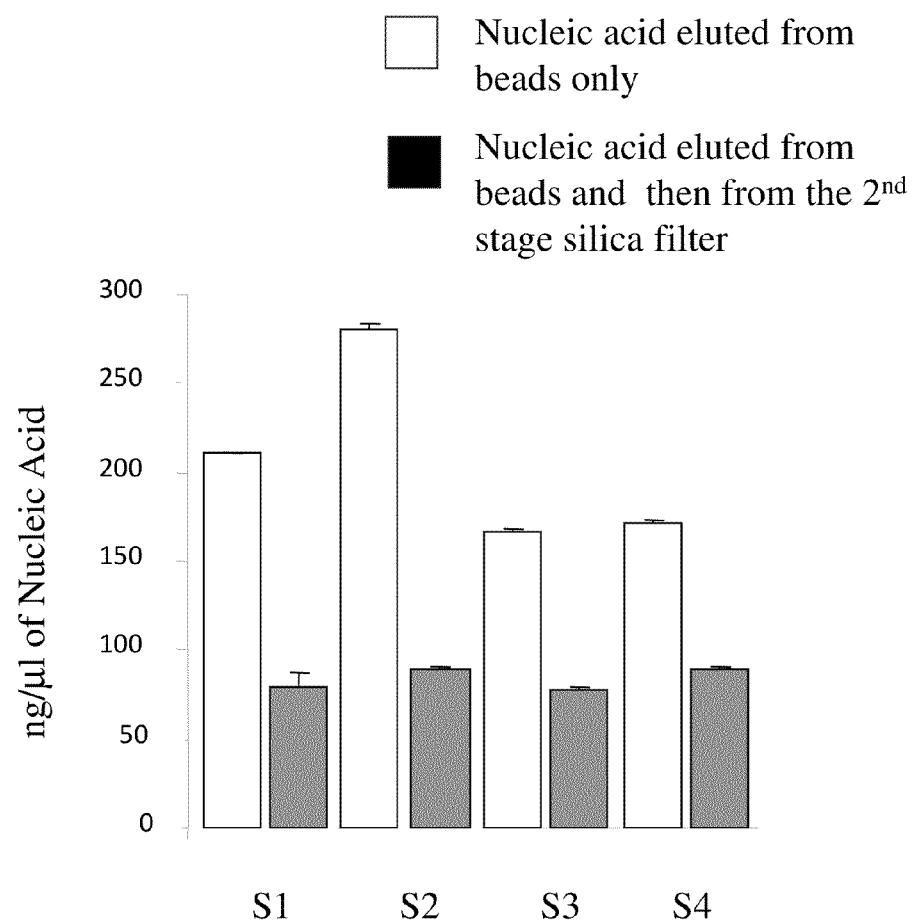

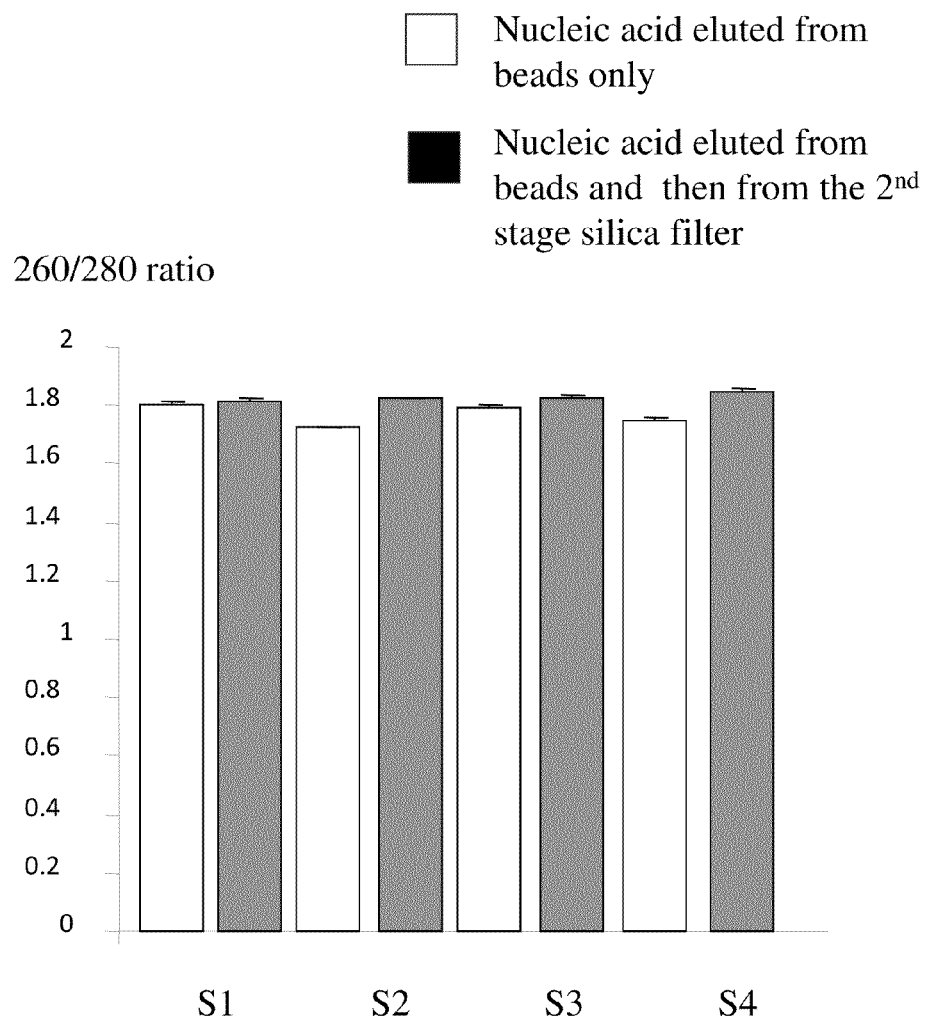

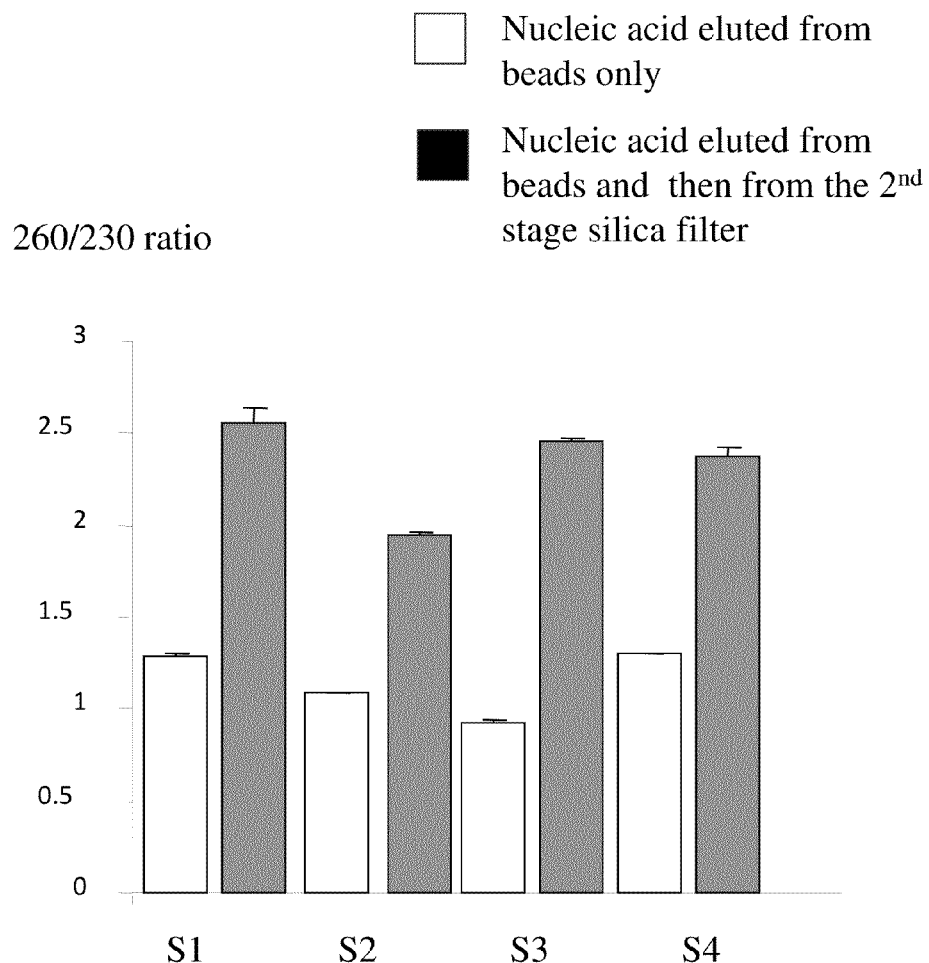

MICROFLUIDIC DEVICE-BASED NUCLEIC ACID PURIFICATION METHOD

CROSS-REFERENCE TO RELATED APPLICATION

This application is a divisional of U.S. application Ser. No. 13/400,857, filed on Feb. 21, 2012, and entitled "Microfluidic Device-Based Nucleic Acid Purification Method," which claims priority to U.S. Provisional Patent Application No. 61/444,952 filed on Feb. 21, 2011, the entire disclosures of which are hereby incorporated herein by reference.

STATEMENT OF GOVERNMENT INTEREST

N/A.

BACKGROUND

1. Field of the Invention

Embodiments of the invention are directed generally to methods for preparing, purifying, amplifying, and detecting biological molecules of interest such as nucleic acids and, more particularly, to such methods performed using microfluidic devices.

2. Description of the Related Art

The use of molecular diagnostics has expanded greatly since its inception in the early 1980s, particularly as a means to permit the detection of slow growing or fastidious bacteria responsible for infectious diseases. The detection of viral pathogens, including viral load testing has also been significantly improved by molecular diagnostics. As more data have become available regarding the human genome, the use of molecular diagnostics in pharmacogenomics, companion diagnostics, and other personalized medicine applications continues to gain momentum.

Nucleic acid amplification is a standard technique known in the art by which nucleic acids may be isolated and more accurately and efficiently manipulated for use in molecular diagnostics and other nucleic acid screening purposes. Various methods have been described in the literature for amplifying nucleic acids, such as deoxyribonucleic acid (DNA) and ribonucleic acid (RNA), present in a sample. Among these, the most widely practiced is the polymerase chain reaction (PCR), described in U.S. Pat. No. 4,683,195 (Mullis et al., entitled "Process for amplifying, detecting, and/or -cloning nucleic acid sequences," issued Jul. 28, 1987) and U.S. Pat. No. 4,683,202 (Mullis, entitled "Process for amplifying nucleic acid sequences," issued Jul. 28, 1987). Briefly, PCR consists of amplifying denatured, complementary strands of target nucleic acid by annealing each strand to a short oligonucleotide primer, wherein the primers are chosen so as to flank the sequence of interest. The primers are then mediated by a polymerase enzyme to yield extension products that are themselves complementary to the primers and hence serve as templates for synthesis of additional copies of the target sequence. Each successive cycle of denaturation, primer annealing, and primer extension essentially doubles the amount of target synthesized in the previous cycle, resulting in exponential accumulation of the target.

PCR methodologies in general suffer from several limitations that are well-known in the art. One such limitation is owing to the poor fidelity of commonly used, thermostable polymerase enzymes, such as Taq. This results in nucleotide base misincorporations that are propagated from one cycle to the next. It is estimated that such misincorporations may occur as often as once per one thousand bases of incorporation. A second limitation is that different cDNAs are amplified with different efficiencies, resulting in underrepresentation of some cDNA sequences and overrepresentation of others in the amplified product. Even a small difference in efficiency may result in a several-thousand fold differential in the representation of these cDNAs in the product after only as few as 30 cycles of amplification.

Another limitation is the presence of inhibitors of PCR in the starting material (e.g., hemoglobin in blood). These inhibitors are often carried through purification and either limit or completely impede amplification reactions performed with the nucleic acids derived from the purification. Therefore this provides another rationale for needing better upstream purification strategies (see e.g., J. Bessetti, Profiles in DNA, PCR Inhibition, An Introduction to PCR Inhibitors, Promega Corporation, March 2007).

Also significant is that nucleic acid amplification is only as accurate as the starting sample of nucleic acid to be amplified. Nucleic acid (e.g., DNA or RNA) of low purity will yield amplification products that may not reflect the composition of the starting sample, and therefore, cannot be used (or relied on) for diagnostic purposes.

It is also recognized that the conventional practice of biochemistry and molecular biology can require physical process resources on a scale that are frequently inversely proportional to the size of the subject being studied. For example, the apparatus and process chemistry associated with the preparation and purification of a biological sample such as a nucleic acid fragment for prospective analysis may easily require a full scale bio-laboratory with sterile facilities. Furthermore, an environmentally isolated facility of similar scale may typically be required to carry out the known nucleic acid amplification procedures such as polymerase chain reaction (PCR) for amplifying the nucleic acid fragment.

There is therefore a need in the art for improved methods of nucleic acid purification for use in nucleic acid amplification techniques, so that nucleic acids may be more accurately and efficiently purified, identified and manipulated for use in molecular diagnostics and other nucleic acid screening purposes. There also exists a need for improved microfluidic systems for processing fluids for analysis of biological or chemical samples, and in particular, in the detection and analysis of biologically active macromolecules derived from such samples such as DNA, RNA, amino acids and proteins. It is beneficial and advantageous that the systems are mass producible, inexpensive, and preferably disposable; that the systems be simple to operate and that many or substantially all of the fluid processing steps be automated; that the systems be customizable, and be modular such that the system can be easily and rapidly reconfigured to suit various applications in which the detection of macromolecules is desired; and, that the systems be able to provide straightforward and meaningful assay results. A more thorough discussion of the challenges and shortcomings in the art, as well as exemplary solutions that may be utilized in conjunction with the teachings of the instant invention, are disclosed in applicant's copending U.S. application Ser. No. 13/033,165 (Pub. No. US2011/0275058) entitled "Self-contained Biological Assay Apparatus, Methods, and Applications," the subject matter of which is incorporated herein by reference in its entirety.

SUMMARY

An embodiment of the instant invention is a microfluidic device-based method for purifying nucleic acid (e.g., DNA or RNA) from a lysed liquid sample solution. The method includes the steps of providing a suitable microfluidic device;

adding an organic solvent to the lysed solution; adding magnetic beads to the lysed solution; binding the nucleic acid to the beads; separating the nucleic acid-bound magnetic beads from the solution; washing the nucleic acid-bound magnetic beads in a wash solution; separating the washed beads from the wash solution; eluting the nucleic acid from the washed beads; reestablishing an appropriate molecular charge on the eluted nucleic acid; recapturing the nucleic acid from the solution, washing the recaptured nucleic acid with a wash solution; and eluting the recaptured nucleic acid to obtain a purified nucleic acid. As used herein and in the claims, a suitable microfluidic device means a microfluidic device or system (a system generally includes a companion instrument that interfaces with the microfluidic device to control the process steps performed by the microfluidic device) having the capability to support and carry out the disclosed processes and claimed process steps. An exemplary suitable microfluidic device and companion instrument is one such as is disclosed in U.S. application Ser. No. 13/033,165 (id.). Other examples of suitable microfluidic devices and systems are known in the art. For example, the device may be composed of any materials commonly used for the production of microfluidic devices such as but not limited to silicon, glass, quartz, elastomeric materials (e.g. PDMS) and polymers (e.g. polystyrene, acrylics, COC's and others). The microfluidic devices may be produced by any known methods for producing microfluidic systems such as photolithography, embossing, laser etching, machining, injection molding; and the devices may incorporate various materials or be constructed from a single material. The device may incorporate discrete assembled parts or be composed of various layers designed to provide the functions required to perform the method. The microfluidic device may be operated manually or robotically, where all or at least some of the reagents are added to the device during the performance of the purification or, the device may include all of the reagents required for the purification placed in reservoirs and operate fully automatically. Generally the microfluidic device will be associated with an instrument capable of implementing the functions designed into the microfluidic device. According to various non-limiting, exemplary aspects, the method may further include the following steps, features, or characteristics:

the step of reestablishing an appropriate molecular charge on the nucleic acid further comprises the steps of adding a suitable buffer to the eluted nucleic acid and adding an organic solvent to the solution, so that the nucleic acid is capable of binding to a substrate during purification;

manually or robotically adding at least some of the reagents to the microfluidic device to carry out the purification process;

providing the microfluidic device containing all of the necessary reagents to automatically carry out the purification process;

estimating, analyzing, and/or amplifying the purified nucleic acid;

repeating the steps of washing the nucleic acid-bound magnetic beads in a wash solution, and separating the washed beads from the wash solution a desired number of times;

mixing the solution for a time sufficient to bind the nucleic acid to the beads;

performing an RNAse treatment after the step of eluting the nucleic acid from the washed beads to remove RNA and only purify DNA;

performing a DNAse treatment after the step of eluting the nucleic acid from the washed beads to remove DNA and only purify RNA.

Another embodiment of the invention is a microfluidic device-based method for purifying nucleic acid (e.g., DNA or RNA) from a source containing nucleic acids. The method includes the steps of obtaining a liquid sample of the source; lysing the liquid sample to create a liquid sample solution; providing a suitable microfluidic device; adding an organic solvent to the lysed solution; adding magnetic beads to the lysed solution; agitating the solution for a time sufficient to bind the nucleic acid to the beads; separating the nucleic acid-bound magnetic beads from the solution; washing the nucleic acid-bound magnetic beads in a wash solution; separating the washed beads from the wash solution; eluting the nucleic acid from the washed beads; reestablishing an appropriate molecular charge on the eluted nucleic acid; capturing the nucleic acid from the solution; and eluting the captured nucleic acid to obtain a purified nucleic acid. According to various non-limiting, exemplary aspects, the method may further include the following steps, features, or characteristics:

the step of reestablishing an appropriate molecular charge on the nucleic acid further comprises the steps of adding a suitable buffer to the eluted nucleic acid and adding an organic solvent to the solution, so that the nucleic acid is capable of binding to a substrate during purification;

manually or robotically adding at least some of the reagents to the microfluidic device to carry out the purification process;

providing the microfluidic device containing all of the necessary reagents to automatically carry out the purification process;

estimating, analyzing, and/or amplifying the purified nucleic acid;

repeating the steps of washing the nucleic acid-bound magnetic beads in a wash solution, and separating the washed beads from the wash solution a desired number of times;

performing an RNAse treatment after the step of eluting the nucleic acid from the washed beads to remove RNA and only purify DNA;

performing a DNAse treatment after the step of eluting the nucleic acid from the washed beads to remove DNA and only purify RNA.

BRIEF DESCRIPTION OF THE DRAWINGS

FIG. 1 is a flow diagram of a microfluidic device-based process for purifying nucleic acid (e.g., DNA or RNA) from a source containing nucleic acids, according to an exemplary embodiment of the invention;

FIG. 4 shows the results, in nanograms per microliter (ng/μl) of eluted DNA, obtained from an exemplary suitable microfluidic device that performs the embodied method for purification of nucleic acids from a biological sample, according to an illustrative aspect of the invention;

FIG. 5 shows the results from subjecting the eluted DNA to analytical ultraviolet light ($\lambda=260$ nm; $\lambda=280$ nm) from DNA obtained from an exemplary suitable microfluidic device that performs the embodied method for purification of nucleic acids from a biological sample, according to an illustrative aspect of the invention;

FIG. 6 shows the results from subjecting the eluted DNA to analytical ultraviolet light (X=260 nm; X=230 nm) from DNA obtained from an exemplary suitable microfluidic device that performs the embodied method for purification of nucleic acids from a biological sample, according to an illustrative aspect of the invention;

DETAILED DESCRIPTION OF NON-LIMITING, EXEMPLARY EMBODIMENTS OF THE INVENTION

FIG. 1 shows a flow diagram 100 of a microfluidic device-based process for purifying nucleic acid (e.g., DNA or RNA) from a source containing nucleic acids. The process is carried out in a suitable microfluidic device as follows.

Figure 2A:
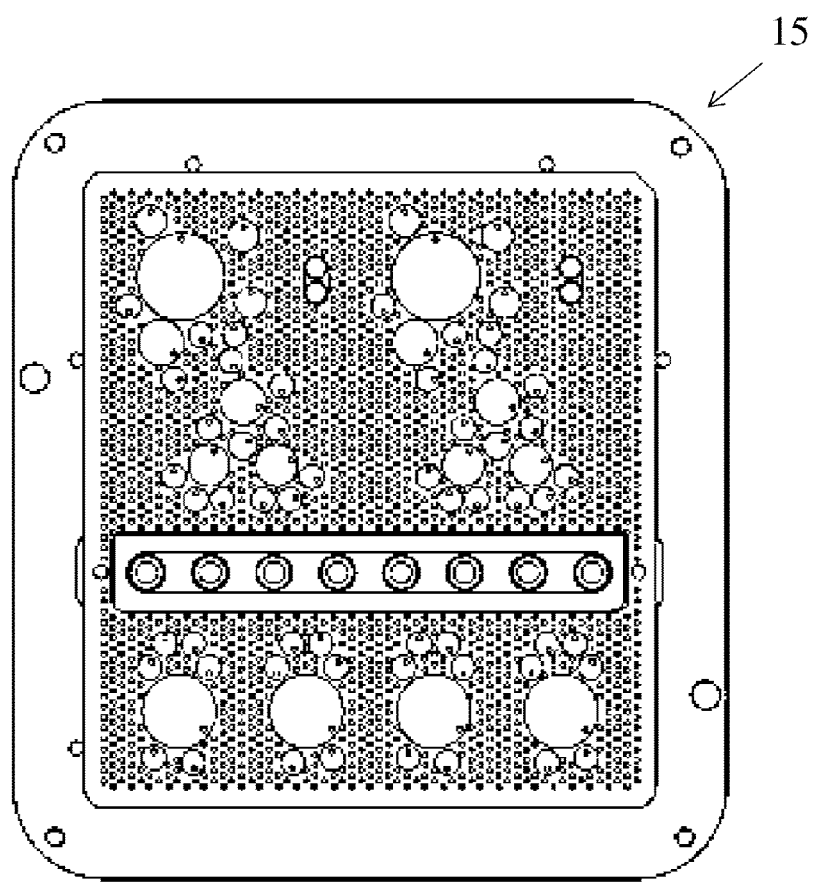
FIGS. 2A, B show a control interface component of an instrument for controlling the actions of an exemplary suitable microfluidic device that performs the embodied method for purification of nucleic acids from a biological sample, according to an illustrative aspect of the invention.

FIGS. 2A and B show a control interface component 15 of an exemplary suitable microfluidic system (hereinafter, 'microfluidic device') that controls the performance of the microfluidic device used in the nucleic acid purification process, which incorporates silica coated magnetic beads as the media that captures nucleic acids liberated from the lysed biological sample (see U.S. application Ser. No. 13/033,165 (Pub. No. US2011/0275058, id.).

Figure 2B:
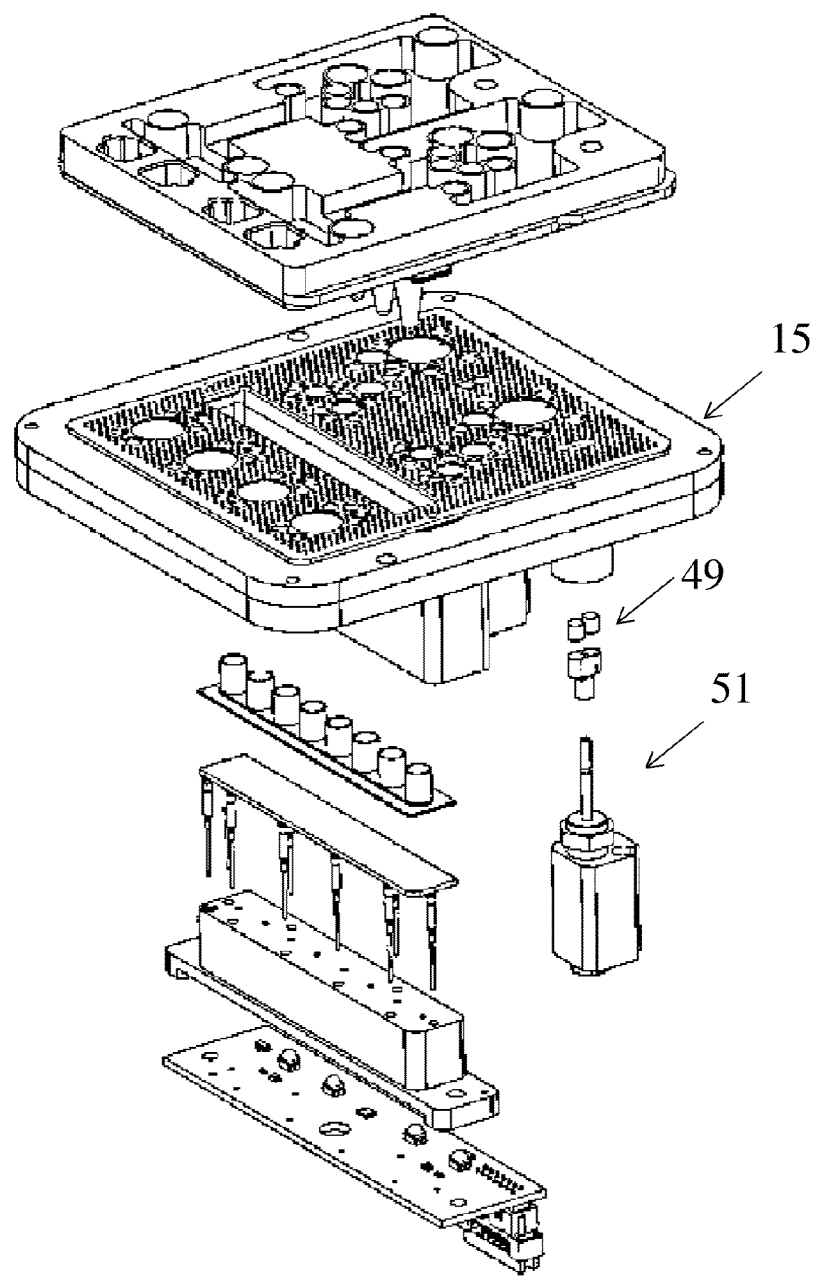
Figure 3A:
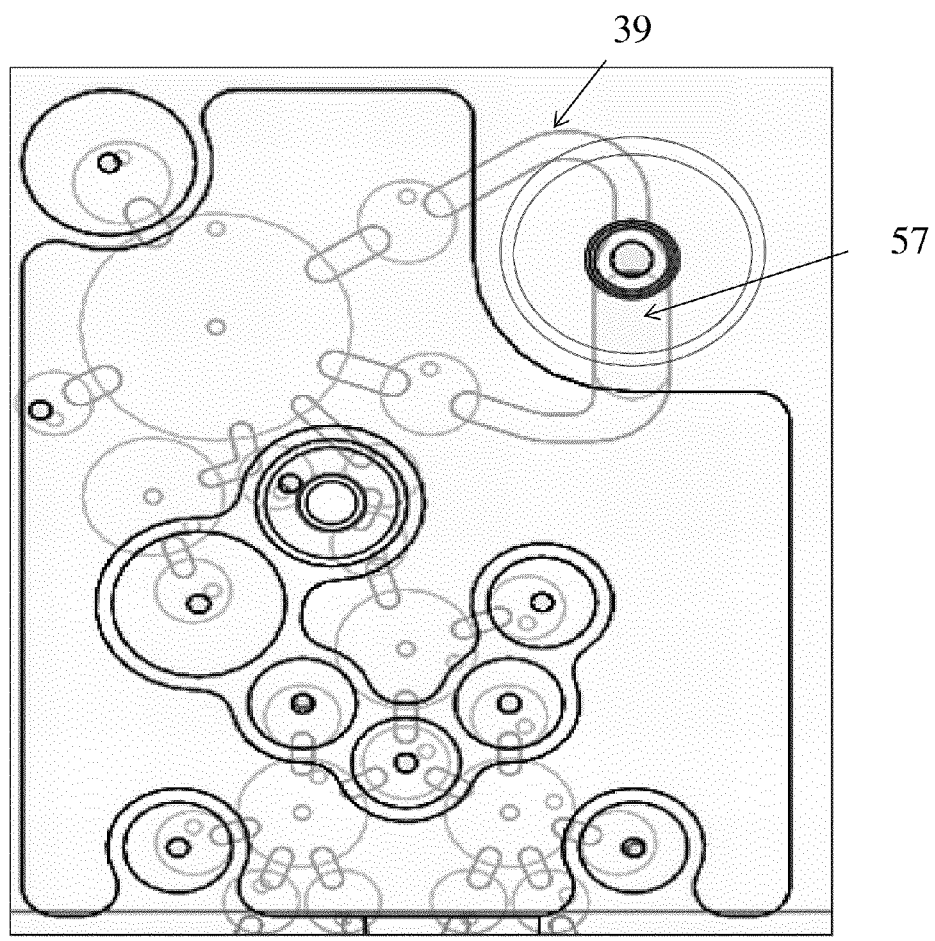
FIGS. 3A-G show an exemplary suitable microfluidic device that performs the embodied method for purification of nucleic acids from a biological sample, according to an illustrative aspect of the invention.

FIG. 3A shows a layered top view of an exemplary suitable microfluidic system (hereinafter, 'microfluidic device') for carrying out the embodied method, that interfaces with control interface 15 incorporating a selectively activated magnet assembly 51 (FIG. 2B) targeting a magnetic separation/concentration channel area 57 and fluidic channels 39 of the microfluidic device.

Figure 3B:
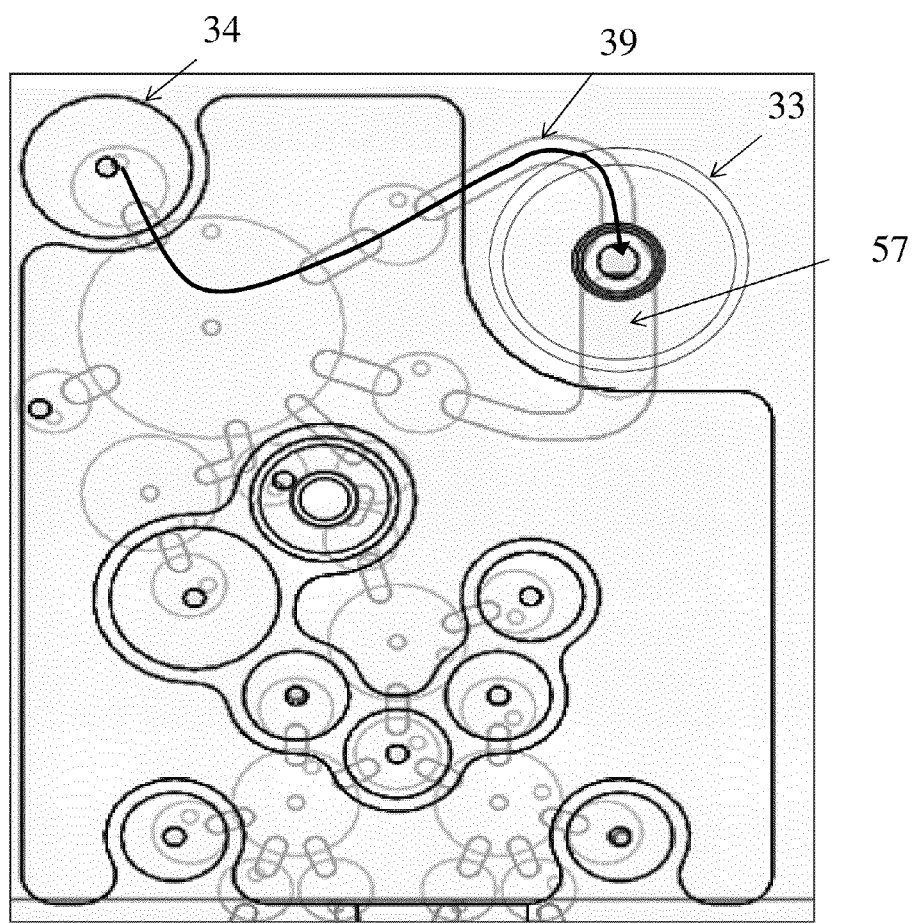

FIGS. 3B-G further illustrate an exemplary nucleic acid purification processes as follows. Referring to FIG. 3B, a biological sample is placed into sample input reservoir 33. An enzyme is dispensed (manually or automatically) into common reagent reservoir 34 and pumped to sample input reservoir 33, then incubated with gentle agitation. A lysis buffer is dispensed into common reagent reservoir 34 and pumped to sample input reservoir 33, then incubated with gentle agitation. Magnetic beads are dispensed into common reagent reservoir 34 and pumped to sample input reservoir 33, then incubated with gentle agitation. An organic alcohol (e.g. isopropanol) is dispensed into common reagent reservoir 34 and pumped to sample input reservoir 33, then incubated with gentle agitation, resulting in the magnetic beads capturing the nucleic acids liberated from the cells in the original biological sample.

Figure 3C:
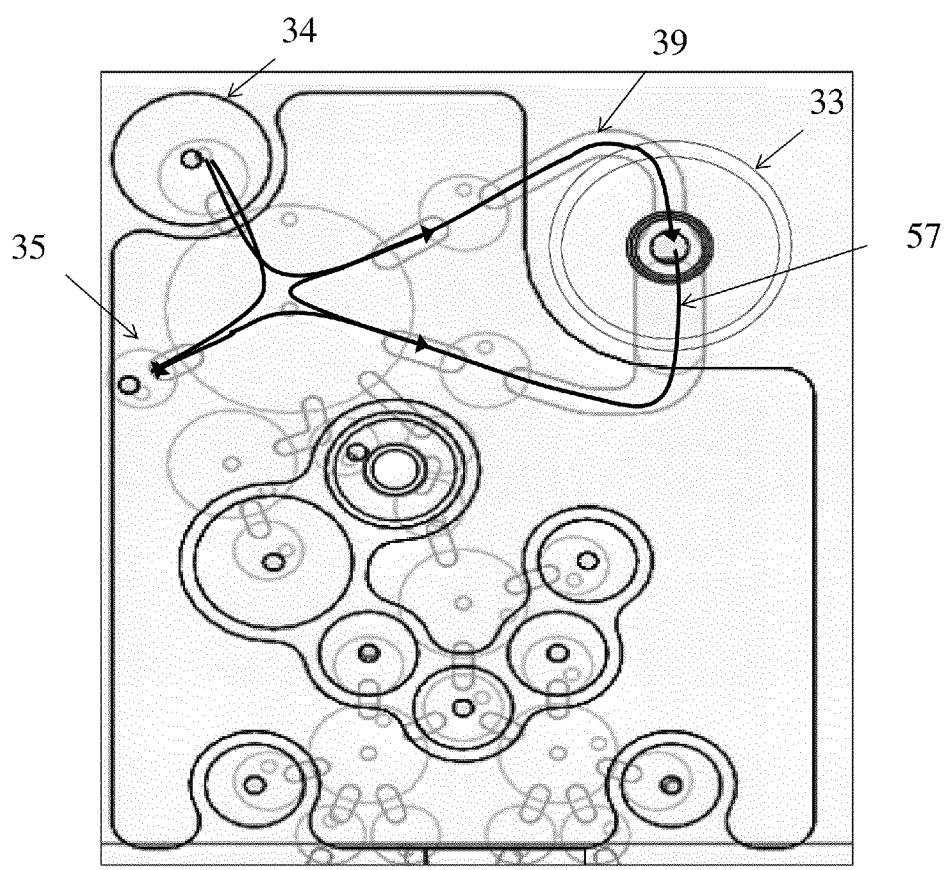

With further reference to FIGS. 2B and 3C, magnet 49 is raised into place under separation/concentration channel 57 and the lysed biological sample solution is pumped to waste reservoir 35 through separation/concentration channel 57 where the magnetic beads with the captured nucleic acids are captured in separation/concentration channel 57 by the magnetic field generated by magnet 49. Magnet 49 is then lowered out of place under separation/concentration channel 57 to remove the magnetic field that captured the magnetic beads.

Then, dispense a wash buffer into common reagent reservoir 34 (preparation), pump to separation/concentration channel 57, and circulate alternatively clockwise/counterclockwise multiple times through separation/concentration channel 57 to re-suspend and wash the beads. Raise magnet 49 into place under separation/concentration channel 57 and pump the solution containing the washed beads to waste reservoir 35 through separation/concentration channel 57 where the magnetic beads with the captured nucleic acids are captured in separation/concentration channel 57 by the magnetic field generated by magnet 49. Lower magnet 49 out of place under separation/concentration channel 57 to remove the magnetic field that captured the magnetic beads. Dispense the same or another wash buffer into common reagent reservoir 34 (preparation), pump to separation/concentration channel 57, and circulate alternatively clockwise/counterclockwise multiple times through separation/concentration channel 57 to re-suspend and wash the beads. Raise magnet 49 into place under separation/concentration channel 57 and pump the solution containing the washed beads to waste reservoir 35 through separation/concentration channel 57 where the magnetic beads with the captured nucleic acids are captured in separation/concentration channel 57 by the magnetic field generated by magnet 49. Continue the above wash steps for the number of repetitions required by the assay. Dispense elution buffer into common reagent reservoir 34 (preparation) and pump it to waste reservoir 35 to clear any residual reagents from the reservoir, channels, and diaphragms of the preparation area. Lower magnet 49 and dispense elution buffer into common reagent reservoir 34 (preparation) and pump it to separation/concentration channel 57, and circulate alternatively clockwise/counterclockwise multiple times through separation/concentration channel 57 to elute the nucleic acids from the beads. Raise magnet 49 into place under separation channel 57 and pump the solution containing the eluted nucleic acids to common reagent reservoir 34 (preparation) through separation/concentration channel 57 where the magnetic beads are captured in separation/concentration channel 57 by the magnetic field generated by magnet 49.

Figure 3D:
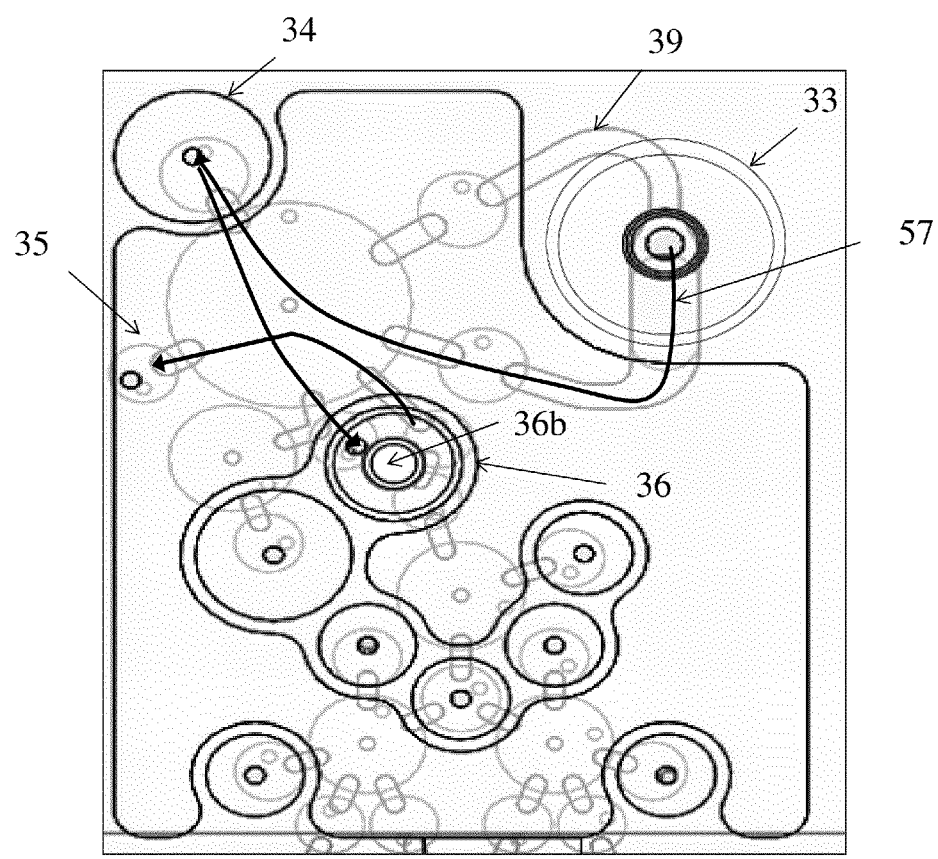

With further reference to FIG. 3D, once the solution containing the eluted nucleic acids is pumped into common reagent reservoir (34), dispense a high salt buffer into common reagent reservoir 34 (preparation). Dispense an organic alcohol (e.g., ethanol) into common reagent reservoir 34 (preparation) so that the eluted nucleic acids now have a reestablished molecular charge so that the nucleic acids are capable of binding to an appropriate substrate for further purification. Pump the contents of common reagent reservoir 34 (preparation), which now contains eluted nucleic acids with an appropriate molecular charge reestablished onto the top of the silica filter 36b in silica filter reservoir 36, pull the contents through silica filter 36b in silica filter reservoir 36 so that the nucleic acids bind to the silica filter, and pump the remaining solution to waste reservoir 35.

Figure 3E:
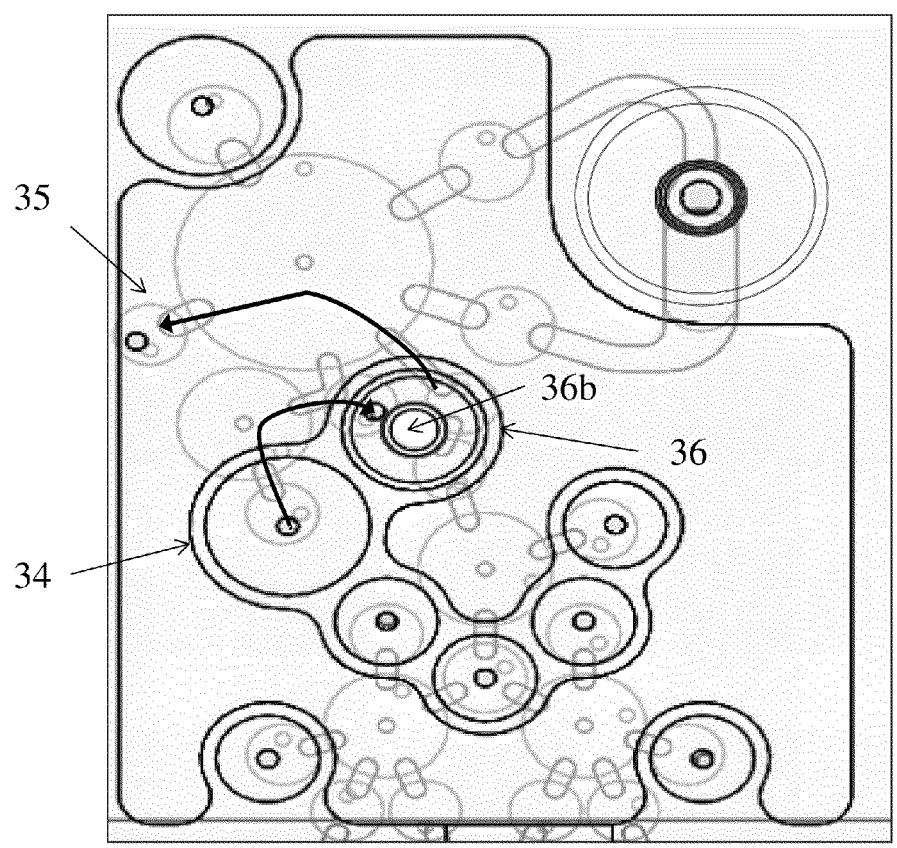

With further reference to FIG. 3E, dispense the same or another wash buffer into common reagent reservoir 34 (elution), pump onto the top of the silica filter 36b in silica filter reservoir 36, pull the contents through silica filter 36b in silica filter reservoir 36, and pump to waste reservoir 35. Repeat with the same or an alternative wash buffers as required by the assay.

Figure 3F:
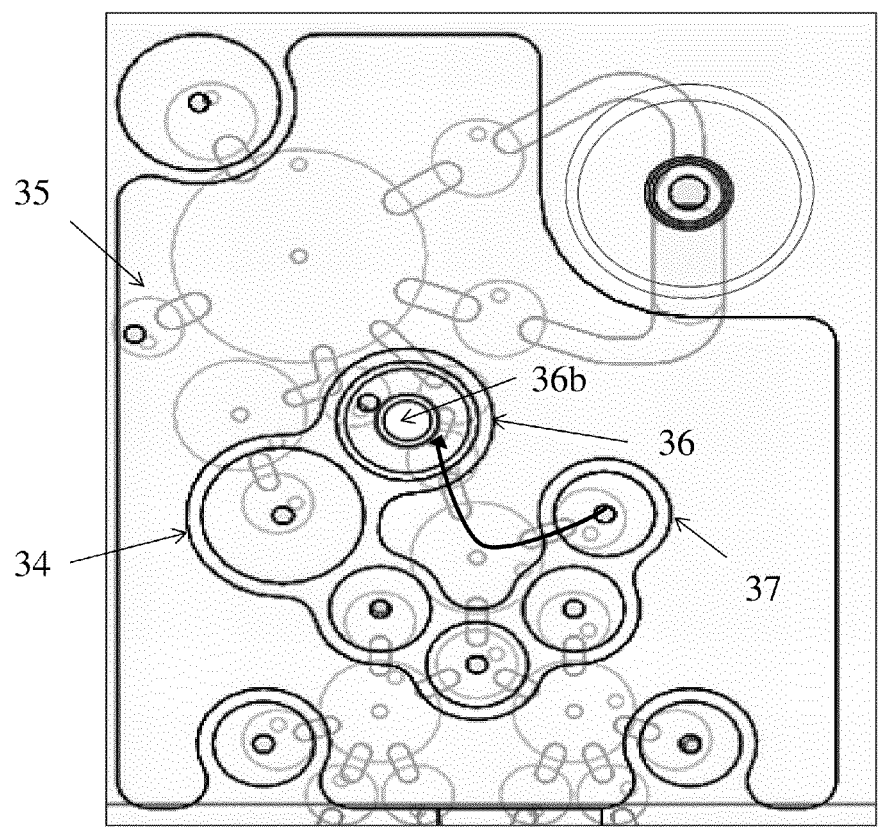

With further reference to FIG. 3F, dispense elution buffer into reservoir 37 (elution) and pump it up through the bottom of the silica filter 36b in silica filter reservoir 36.

Figure 3G:
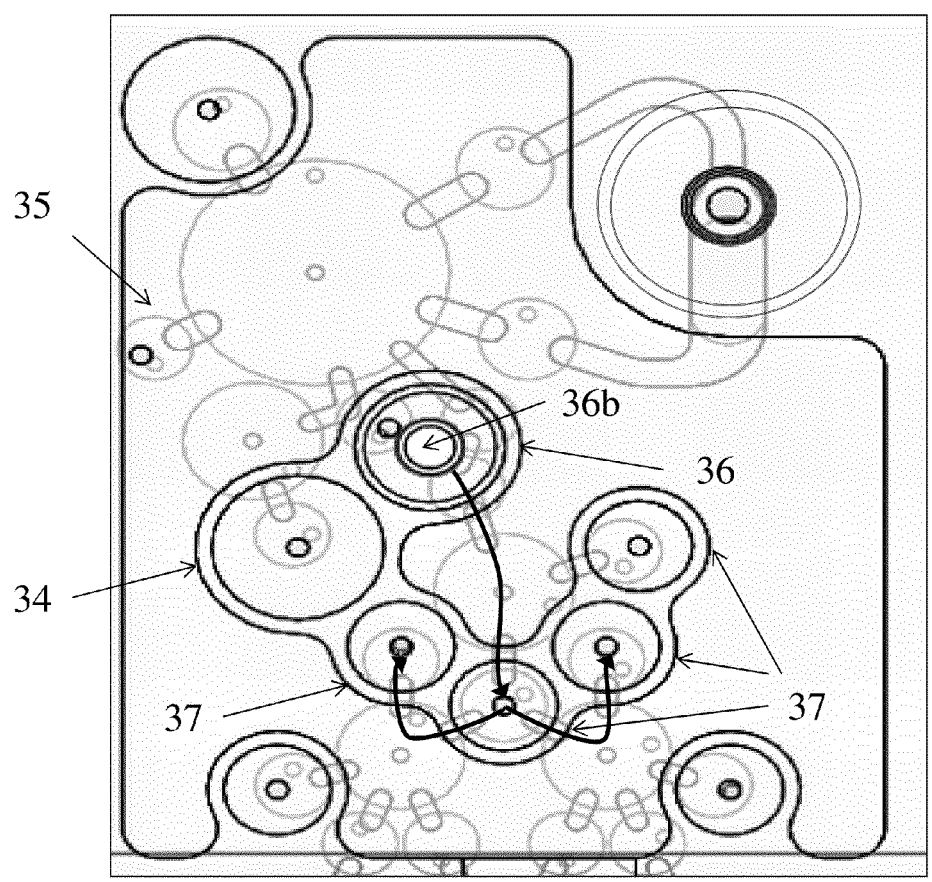

With further reference to FIG. 3G, pull the contents of silica filter reservoir 36 that now contains eluted nucleic acids through the silica filter, pump it to elution reservoir 37 (center), and then equally to elution reservoir 37L and 37R; or alternatively, pump it directly in equal amounts to reservoir 37L and 37R by bypassing elution reservoir 37 (center). The eluted nucleic acids are then in condition for further analysis or amplification. The nucleic acids purified in this manner contain lower concentrations of impurities that inhibit amplification reactions commonly performed using purified nucleic acids.

Figure 7:
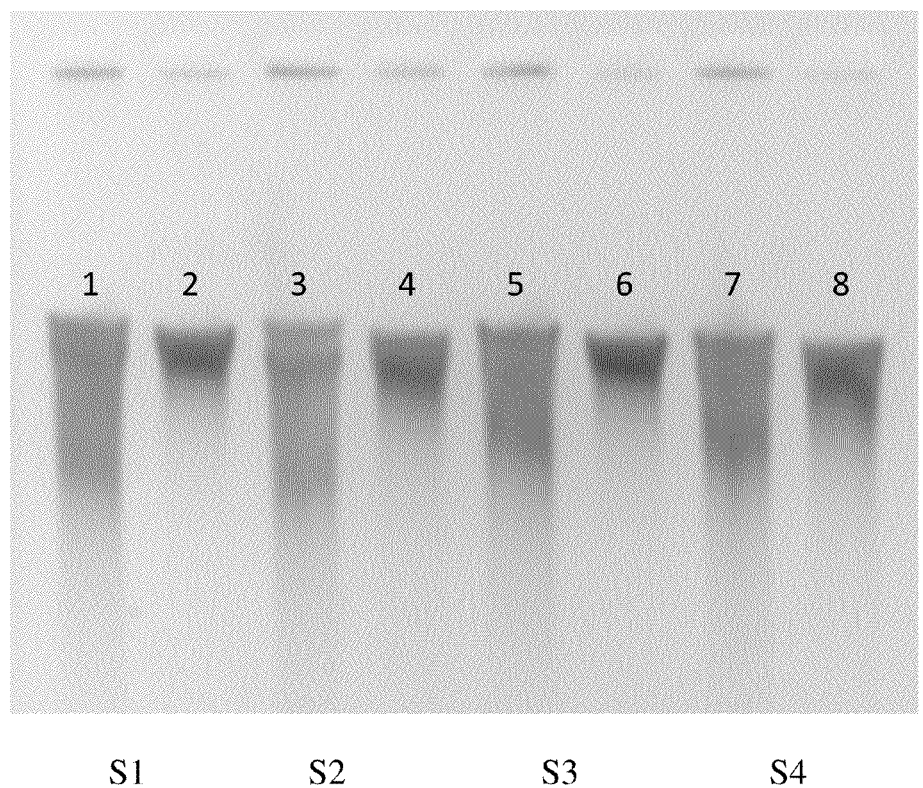
FIG. 7 shows electrophoretic gel results from DNA obtained from an exemplary suitable microfluidic device that performs the embodied method for purification of nucleic acids from a biological sample, according to an illustrative aspect of the invention.
Figure 8:
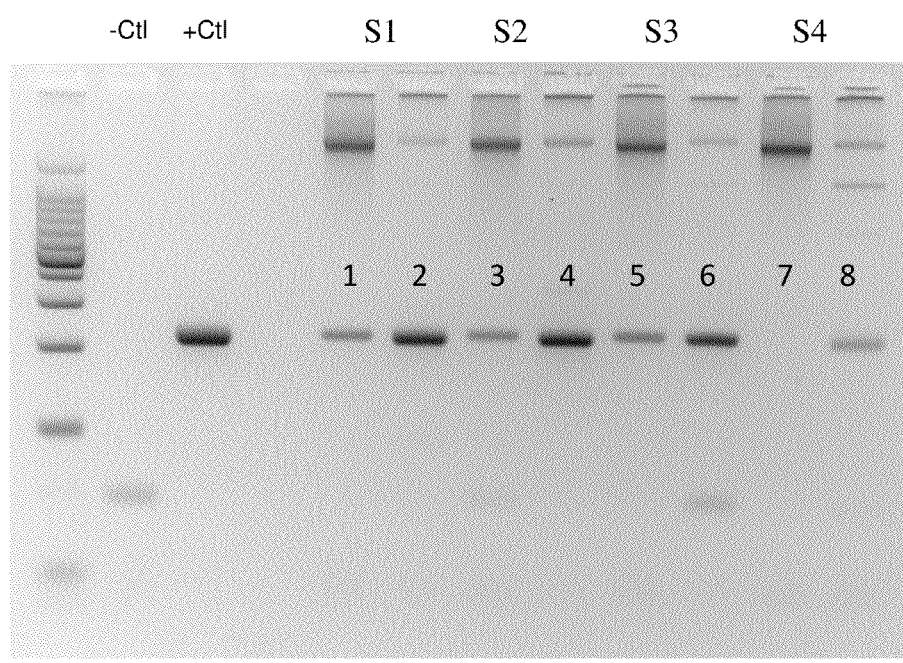
FIG. 8 shows electrophoretic gel results from DNA obtained from an exemplary suitable microfluidic device that performs the embodied method for purification of nucleic acids from a biological sample, according to an illustrative aspect of the invention.

FIGS. 4-8 show results obtained by using the microfluidic device to carry out the embodied nucleic acid purification method. More particularly, FIG. 4 shows a nucleic acid recovery estimate of four individually purified samples (S1 to S4) by A260 UV measurement; and, a greater recovery using only the beads, which is the result losing a portion of the originally recovered nucleic acid during the subsequent purification. Importantly, the second elution provides a suitably large amount of DNA for customary DNA analysis and amplification. FIG. 5 shows a common nucleic acid purity estimate of four individually purified samples (S1 to S4) by A260/A280 UV measurement. As expected from traditional practice with the bead only method, the A260/A280 method would provide measurably pure nucleic acid by this measurement; the measurement, though, does not capture certain contaminants actually present in the bead only sample. In FIG. 6, a nucleic acid purity estimate of four individually purified samples (S1 to S4) by A260/A230 UV measurement is shown, and illustrates significant improvement in purity from the second purification. The A260/A230 measurement does capture the presence of certain contaminants that are not measurable using the A260/A280 measurement. The purity achieved is the result of removing a greater amount of the inhibitors (especially those associated with nucleic acid purification from whole blood). FIG. 7 shows gel electrophoresis of genomic DNA from whole blood Samples (S1 to S4). Lanes 1, 3, 5, and 7 samples were eluted from bead only purification, while lanes 2, 4, 6, and 8 samples were eluted from bead and then the silica column. The trails are smaller DNA fragments and larger amounts of RNA present in the bead only purification samples. FIG. 8 shows gel electrophoresis of PCR amplicons from whole blood Samples (S1 to S4). Lanes 1, 3, 5, and 7 samples were eluted from bead only purification, while lanes 2, 4, 6, and 8 samples were eluted from bead and then the silica column. The darker and more intense bands in lanes 2, 4, 6, and 8 indicate amplification from a more pure DNA elution with reduced inhibitors and carryover of purification chemistry.

The method embodiments disclosed herein can be used to purify nucleic acids from any source known in the art that comprises nucleic acids, such as prokaryotic or eukaryotic organisms, viruses, cell, tissues, organs, etc. In an illustrative aspect, the tissue is whole blood. In another illustrative aspect, the sample is liquefied or is dissolved in a liquid. In another illustrative aspect, the method eliminates the step of culturing (or growing) cells or organisms containing a nucleic acid of interest prior to nucleic acid purification.

According to an exemplary aspect, the method for purifying nucleic acid (e.g., DNA) can be preceded by the preparatory steps as follows: lysing the liquid sample, (e.g., by adding lyticase or lysozyme enzyme or other suitable lytic enzyme, chaotropic agent, sonication, laser lysis or another lysing system known in the art to have similar properties, and optionally adding RNAse or DNAse treatment in a suitable microfluidic device thereby forming a solution comprising the liquid sample and cellular components; agitating the solution; incubating the solution at a suitable temperature, e.g., at room temperature; adding proteinase K (or other proteinase known in the art to have similar properties) to the solution; agitating the solution; incubating the solution at a suitable temperature, e.g., at room temperature or up to 55° C.; adding an art-known lysis/binding buffer to the solution (any lysis buffer/binding buffer known in the art can be used, provided that it is optimized (using art known methods) for nucleic acid binding to the purification matrix); agitating the solution; incubating the solution, e.g., at room temperature; adding magnetic beads to the solution (any suitable magnetic beads known in the art can be used, wherein the beads are coated with a silica-like chemistry that allows the nucleic acid to bind; (e.g., Invitrogen, Dynabeads® MyOne™ SILANE); and again agitating the solution. Such preparatory steps may be conducted on standard bench top equipment or in a microfluidic chip that is the same chip or a different chip than the chip conducting the purification.

After the above preparatory steps are conducted, the purification method can be conducted, comprising the following steps: adding about an equal volume of a suitable, art-known organic solvent (e.g., isopropyl alcohol) to the solution; agitating the solution; incubating the solution at a suitable temperature, e.g., at room temperature; collecting the magnetic beads, e.g., by placing a magnet on the outside of the container or microfluidic system; removing the supernatant using the microfluidic device; adding a suitable art-known wash buffer optimized for nucleic acid (e.g., DNA) binding to the magnetic beads (for silica based binding, wash buffers typically include a chaotropic and non-chaotropic salt, pH buffer, ethanol, and optionally, detergent. Any buffer and wash system that is compatible with nucleic acid binding to silica can be used, provided that the combination has been optimized for the system using art-known methods); agitating the solution to re-suspend the beads; collecting the beads; optionally, repeating the steps of adding the wash buffer to the magnetic beads, agitating the solution to re-suspend the beads, and collecting the beads (the residual liquid left in the container prior to DNA elution can be removed so that any buffer and/or organic solvent contamination or interference with elution is removed); adding a suitable art-known nucleic acid elution buffer (e.g., nuclease-free water); agitating the solution; incubating the solution at a suitable temperature, e.g., at room temperature to elute the nucleic acid (e.g., DNA) bound to the magnetic beads (in this exemplary aspect, RNAse treatment is not included since total nucleic acid (including a desired DNA of interest) is being bound and eluted; rather, only the DNA present is analyzed. Alternatively, an RNAse treatment step could be included to remove RNA if desired or, a DNAse step to remove all DNA to only purify RNA); collecting the beads, e.g., by placing a magnet on the outside of the container or microfluidic system; adding a suitable nucleic acid lysis/binding buffer to the eluted DNA; agitating the solution; adding about an equal volume of suitable, art-known organic solvent (e.g., absolute ethanol) to the solution; agitating the solution; transferring the solution to a nucleic acid purification column or filter (any suitable column or filter for purifying nucleic acid known in the art can be used. In an exemplary aspect, a silica filter is used in the microfluidic device); eluting purified nucleic acid (e.g., DNA) from the purification column or filter; and collecting the eluted nucleic acid (e.g., DNA).

Once the eluted, purified nucleic acid from the above-described method for purifying nucleic acid is collected, the purified nucleic acid can be, e.g., estimated, run on a standard gel for genomic DNA analysis, and/or subjected to PCR amplification or other nucleic acid amplification methods known in the art, e.g., to amplify a target gene.

The embodied method for purifying nucleic acid can be adapted to be automated and run in the microfluidic device. For example, in U.S. application Ser. No. 13/033,165 (id.), FIGS. 24A-24K and FIG. 25 show the flow of solution during a two-stage DNA purification conducted on a microfluidic device.

Example 1

Protocol for Method for Purifying DNA from Whole Blood

This example describes a non-limiting, exemplary method for purifying DNA from whole blood.

1) Add 124 units of Lyticase enzyme to 500 µl of whole blood and agitate the solution. Incubate the sample at room temperature for 30 minutes.

2) Add 71.4 µl 20 mg/ml proteinase K to the sample, briefly agitate the solution, and incubate the sample at room temperature for 2 minutes.

3) Add 500 µl of lysis/binding buffer to the sample, agitate the solution and incubate at room temperature for 10 minutes.

4) Add 25 µl of magnetic beads to the sample and agitate for 30 seconds.

5) Add 571 µl of isopropyl alcohol, agitate, and incubate for 5 minutes at room temperature while agitating.

6) Collect the beads by placing a magnet on the outside of the tube, channel or reservoir and carefully remove the supernatant using a microfluidic system. Dispose of supernatant.

7) Add 950 µl of wash buffer to the magnetic beads and agitate the solution to resuspend the beads. Collect the beads and dispose of the supernatant.

8) Repeat step 7.

9) Add 950 µl of wash buffer 2 to the magnetic beads and agitate the solution to resuspend the beads. Collect the beads and dispose of the supernatant.

10) Remove any residual liquid left in the tube, channel or reservoir prior to DNA elution to avoid organic solvent contamination.

11) Add 100 µl of nuclease-free water, agitate the solution, and incubate at room temperature for two minutes to elute the DNA bound to the magnetic beads.

12) Collect the beads by placing a magnet on the outside of the tube, channel or reservoir and carefully transfer the supernatant to the second stage.

13) Add 100 µl of nucleic acid lysis/binding buffer to the 100 µl of eluted DNA and agitate the solution.

14) Add 100 µl of absolute ethanol and agitate the solution.

15) Transfer the solution to a silica filter insert that is placed in a tube, channel or reservoir of the microfluidic system.

16) Pump the solution through the silica filter.

17) Pump 200 µl of wash buffer through the silica filter.

18) Pump another 200 µl of wash buffer through the silica filter.

19) Pump 50 µl of nuclease-free water backwards through the silica filter then reverse the direction of the fluid and collect the eluted DNA when the fluid exits the silica filter.

The purified DNA may then be estimated, run on a gel for genomic DNA analysis, and/or subjected to PCR amplification or other suitable amplification system to amplify target gene(s).

All references, including publications, patent applications, and patents cited herein are hereby incorporated by reference in their entireties to the same extent as if each reference was individually and specifically indicated to be incorporated by reference and was set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein is merely intended to serve as a shorthand method of referring individually to each separate value falling within the range, unless otherwise indicated herein, and each separate value is incorporated into the specification as if it was individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents. Therefore, the embodiments are illustrative of the invention rather than limiting of the invention. Revisions and modifications may be made to methods, materials, structures and dimensions in accordance with the embodiments.

We claim:

1. A microfluidic device-based method for purifying nucleic acid from a lysed liquid sample solution, comprising:
   providing a suitable microfluidic device comprising a first purification matrix and a second purification matrix;
   performing a first purification step using the first purification matrix, the first purification step comprising the steps of:
   adding an organic solvent to the lysed solution;
   adding a first capture medium to the lysed solution;
   capturing the nucleic acid to the first capture medium;
   separating the nucleic acid-bound first capture medium from the solution;
   washing the nucleic acid-bound first capture medium with a wash solution;
   separating the washed first capture medium from the wash solution; and
   eluting the nucleic acid from the washed first capture medium;
   performing a second purification step using the second purification matrix, the second purification step comprising the steps of:
   reestablishing an appropriate molecular charge on the eluted nucleic acid;
   re-capturing the nucleic acid from the solution using a second capture medium;

washing the re-captured nucleic acid with a wash solution; and eluting the re-captured nucleic acid to obtain a purified nucleic acid.

2. The method of claim 1, wherein the step of reestablishing an appropriate molecular charge on the nucleic acid further comprises the steps of adding a suitable buffer to the eluted nucleic acid and adding an organic solvent to the solution.

3. The method of claim 1, further comprising adding at least some of the reagents to the microfluidic device to carry out the purification process.

4. The method of claim 1, further comprising providing the microfluidic device containing all of the necessary reagents to automatically carry out the purification process.

5. The method of claim 1, further comprising at least one of estimating, analyzing, and amplifying the purified nucleic acid.

6. The method of claim 1, further comprising repeating the steps of washing the nucleic acid-bound first capture medium in a wash solution, and separating the washed first capture medium from the wash solution a desired number of times.

7. The method of claim 1, further comprising performing an RNAse treatment after the step of eluting the nucleic acid from the washed first capture medium to remove RNA and only purify DNA.

8. The method of claim 1, further comprising performing a DNAse treatment after the step of eluting the nucleic acid from the washed first capture medium to remove DNA and only purify RNA.

9. A microfluidic device-based method for purifying nucleic acid from a source containing nucleic acids, comprising:

obtaining a liquid sample of the source;

lysing the liquid sample to create a liquid sample solution;

providing a suitable microfluidic device comprising a first purification matrix and a second purification matrix;

performing a first purification step using the first purification matrix, the first purification step comprising the steps of:

adding an organic solvent to the lysed solution;

adding a first capture medium to the lysed solution;

binding the nucleic acid to the first capture medium;

separating the nucleic acid-bound first capture medium from the solution;

washing the nucleic acid-bound first capture medium in a wash solution;

separating the washed first capture medium from the wash solution; and eluting the nucleic acid from the first capture medium;

performing a second purification step using the second purification matrix, the second purification step comprising the steps of:

re-establishing an appropriate molecular charge on the eluted nucleic acid;

re-capturing the nucleic acid from the solution using a second capture medium;

washing the re-captured nucleic acid with a wash solution; and eluting the re-captured nucleic acid to obtain a purified nucleic acid.

10. The method of claim 9, wherein the step of reestablishing an appropriate molecular charge on the nucleic acid further comprises the steps of adding a suitable buffer to the eluted nucleic acid and adding an organic solvent to the solution.

11. The method of claim 9, further comprising manually adding at least some of the reagents to the microfluidic device to carry out the purification process.

12. The method of claim 9, further comprising providing the microfluidic device containing all of the necessary reagents to automatically carry out the purification process.

13. The method of claim 9, further comprising at least one of estimating, analyzing, and amplifying the purified nucleic acid.

14. The method of claim 9, further comprising repeating the steps of washing the nucleic acid-bound first capture medium in a wash solution, and separating the washed first capture medium from the wash solution a desired number of times.

15. The method of claim 9, further comprising performing an RNAse treatment after the step of eluting the nucleic acid from the washed first capture medium to remove RNA and only purify DNA.

16. The method of claim 9, further comprising performing a DNAse treatment after the step of eluting the nucleic acid from the washed first capture medium to remove DNA and only purify RNA.

* * * * *